United States Patent [19]

Butterworth et al.

[11] 4,425,126

[45] Jan. 10, 1984

[54] FIBROUS MATERIAL AND METHOD OF MAKING THE SAME USING THERMOPLASTIC SYNTHETIC WOOD PULP FIBERS

[75] Inventors: George A. M. Butterworth, Western Springs; Robert T. Elias, Downers Grove; Wayne D. Miller, Naperville; Robert C. Shepherd, Oak Lawn, all of Ill.

[73] Assignee: Johnson & Johnson Baby Products Company, New Brunswick, N.J.

[21] Appl. No.: 196,810

[22] Filed: Oct. 14, 1980

Related U.S. Application Data

[63] Continuation-in-part of Ser. No. 107,945, Dec. 28, 1979, abandoned, which is a continuation of Ser. No. 734,078, Oct. 20, 1976, abandoned.

[51] Int. Cl.³ .............................................. A41B 13/02
[52] U.S. Cl. .................................... 604/366; 428/152; 428/181; 428/198; 428/286; 428/290; 428/296; 428/302; 428/310.5; 428/316.6; 604/367; 604/375; 264/128; 264/119
[58] Field of Search .................. 128/284, 287, 290 W; 428/198, 286, 290, 296, 302, 317, 321, 913; 604/366, 367, 375

[56] References Cited

U.S. PATENT DOCUMENTS

| | | |
|---|---|---|
| 2,045,095 | 6/1936 | Osborne . |
| 2,414,833 | 1/1947 | Osborne . |
| 2,477,000 | 7/1949 | Osborne . |
| 2,626,214 | 1/1953 | Osborne . |
| 2,708,617 | 5/1955 | Mogat . |
| 2,810,646 | 10/1957 | Wooding et al. . |
| 2,825,282 | 3/1958 | Gergen . |
| 2,899,351 | 8/1959 | Morse . |
| 2,962,414 | 11/1960 | Arledter . |
| 2,962,415 | 11/1960 | Arledter . |
| 2,971,858 | 2/1961 | Di Giulio et al. . |
| 2,971,877 | 2/1961 | Arledter . |
| 2,978,446 | 4/1961 | Battista et al. . |
| 2,999,788 | 9/1961 | Morgan . |
| 3,003,912 | 10/1961 | Harford . |
| 3,013,936 | 12/1961 | Iyengas . |
| 3,035,965 | 5/1962 | Mathews . |
| 3,047,455 | 7/1962 | Holmes et al. . |
| 3,047,456 | 7/1962 | Veci et al. . |
| 3,049,466 | 8/1962 | Erlich . |
| 3,052,593 | 9/1962 | Battista . |
| 3,057,772 | 9/1962 | Magill et al. . |
| 3,068,527 | 12/1962 | Morgan . |
| 3,081,519 | 3/1963 | Blades et al. . |
| 3,095,345 | 6/1963 | Jackson et al. . |
| 3,097,991 | 7/1963 | Miller et al. . |
| 3,099,067 | 7/1963 | Merrian . |
| 3,101,294 | 8/1963 | Fridricksen . |
| 3,104,198 | 9/1963 | Brissette . |
| 3,131,088 | 4/1964 | Festag . |
| 3,141,812 | 7/1964 | Marek et al. . |
| 3,141,813 | 7/1964 | Marek et al. . |
| 3,169,899 | 2/1965 | Steuber . |
| 3,193,447 | 7/1965 | Marek et al. . |
| 3,200,033 | 8/1965 | Grossteinbeck . |
| 3,223,581 | 1/1966 | Willicks . |
| 3,227,608 | 1/1966 | Willicks et al. . |
| 3,227,664 | 1/1966 | Blades et al. . |
| 3,271,237 | 9/1966 | Sommer et al. . |
| 3,276,944 | 10/1966 | Levy . |
| 3,282,038 | 11/1966 | Howell . |
| 3,290,207 | 12/1966 | Magat et al. . |
| 3,320,117 | 5/1967 | Aoki et al. . |
| 3,341,394 | 9/1967 | Kinney . |
| 3,350,260 | 10/1967 | Johnson . |
| 3,354,032 | 11/1967 | Sommer et al. . |
| 3,359,155 | 12/1967 | Kojitani . |
| 3,364,102 | 1/1968 | Spence et al. . |
| 3,384,535 | 5/1968 | Marek et al. . |
| 3,385,752 | 5/1968 | Selke et al. . |
| 3,391,057 | 7/1968 | Spence et al. . |
| 3,395,070 | 7/1968 | Adams et al. . |
| 3,401,078 | 9/1968 | Grossteinbeck et al. . |
| 3,402,231 | 9/1968 | Bynum et al. . |
| 3,433,703 | 3/1969 | Riedesel . |
| 3,434,918 | 3/1969 | Bernardin . |
| 3,444,859 | 5/1969 | Kalwaites . |
| 3,485,705 | 12/1969 | Harmon . |
| 3,486,970 | 12/1969 | Troemel et al. . |
| 3,489,643 | 1/1970 | Hoffman . |
| 3,532,800 | 10/1970 | Wyly et al. . |
| 3,539,434 | 10/1970 | Spaulding . |
| 3,542,634 | 11/1970 | Such et al. . |
| 3,551,538 | 12/1970 | Yamamoto et al. . |
| 3,553,302 | 1/1971 | Susuki et al. . |
| 3,560,318 | 2/1971 | Miller et al. . |

| | | |
|---|---|---|
| 3,582,462 | 6/1971 | Ashikaga et al. |
| 3,597,312 | 8/1971 | Kohne et al. |
| 3,599,638 | 8/1971 | Rickard |
| 3,613,687 | 10/1971 | Kennedy |
| 3,660,551 | 5/1972 | Susuki et al. |
| 3,663,348 | 5/1972 | Liloia et al. ............... 428/302 |
| 3,669,829 | 6/1972 | Caldo et al. |
| 3,674,621 | 7/1972 | Miyamoto et al. |
| 3,717,541 | 2/1973 | Schirmer |
| 3,720,572 | 3/1973 | Soda et al. |
| 3,723,236 | 3/1973 | Newman |
| 3,730,667 | 5/1973 | Tani et al. |
| 3,740,797 | 6/1973 | Farrington |
| 3,756,908 | 9/1973 | Gross |
| 3,765,999 | 10/1973 | Toyoda |
| 3,768,118 | 10/1973 | Ruffo |
| 3,772,739 | 11/1973 | Lovgren |
| 3,795,575 | 3/1974 | Gouw |
| 3,804,092 | 4/1974 | Tune |
| 3,808,091 | 4/1974 | Aoki et al. |
| 3,821,074 | 6/1974 | Lin |
| 3,826,712 | 7/1974 | Masuda et al. |
| 3,828,784 | 8/1974 | Zoephel |
| 3,838,694 | 10/1974 | Mesek |
| 3,855,045 | 12/1974 | Brock |
| 3,855,046 | 12/1974 | Hansen et al. |
| 3,856,612 | 12/1974 | McGinnis |
| 3,886,942 | 6/1975 | Bernardin |
| 3,939,836 | 2/1976 | Tune |
| 3,952,124 | 4/1976 | Mesek |
| 3,955,577 | 5/1976 | Gellert |
| 3,973,067 | 8/1976 | Newman |

FOREIGN PATENT DOCUMENTS

| | | |
|---|---|---|
| 933718 | 9/1973 | Canada |
| 7313173 | 3/1974 | Netherlands |
| 697431 | 9/1969 | South Africa |
| 1102342 | 2/1968 | United Kingdom |

*Primary Examiner*—James C. Cannon
*Attorney, Agent, or Firm*—Martha A. Michaels

[57] ABSTRACT

A high loft, low density, nonwoven fibrous web is provided comprising a plurality of irregularly arranged, intersecting, overlapping, mechanically interengaged, loosely assembled fibers including both thermoplastic synthetic wood pulp fibers and other fibers, segments of the thermoplastic synthetic wood pulp fibers being heat fused at a plurality of junctures with segments of other thermoplastic synthetic wood pulp fibers and with segments of fibers of other types, with additional binder distributed throughout the web.

The web is prepared by air-laying a blend of thermoplastic synthetic wood pulp fibers and other fibers applying heat without pressure to the air-laid blend to fuse at least some of the thermoplastic synthetic wood pulp fibers to each other and to some of the other fibers to form a self-supporting fibrous web, introducing a latex binder into the web and drying and curing the binder.

This application relates to a high loft, low density, nonwoven fibrous material, such as an air-laid web or fabric, containing synthetic wood pulp fibers as one constituent thereof, and to a method of producing the same.

48 Claims, 6 Drawing Figures

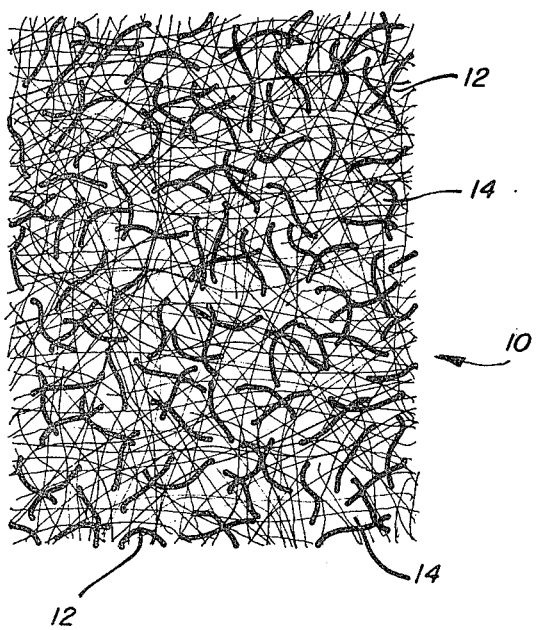
FIG. 1
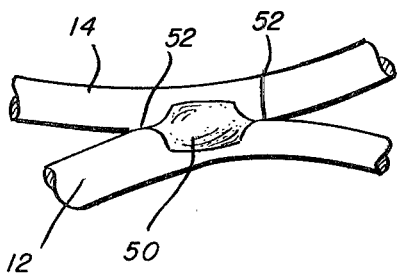
FIG. 3
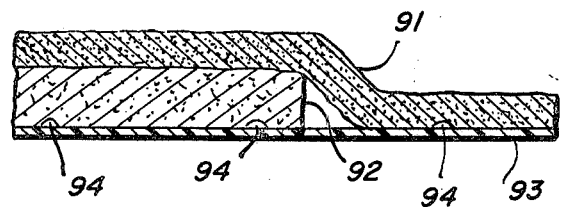
FIG. 6
FIG. 5
FIG. 4
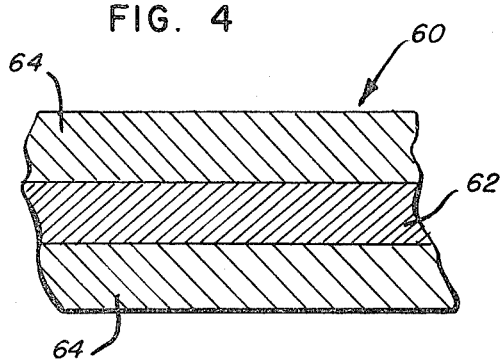
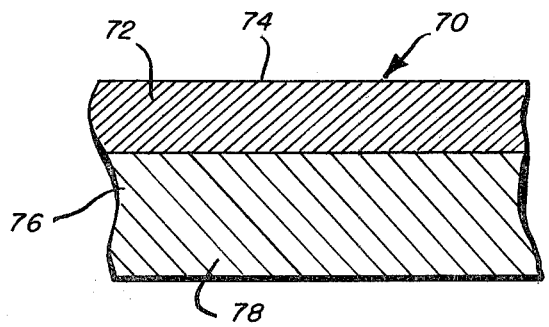
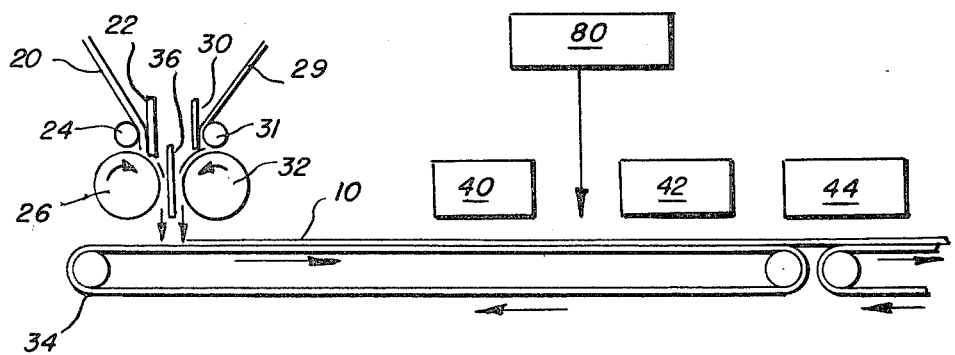
FIG. 2

FIBROUS MATERIAL AND METHOD OF MAKING THE SAME USING THERMOPLASTIC SYNTHETIC WOOD PULP FIBERS

This is a continuation-in-part application of application Ser. No. 107,945, filed Dec. 28, 1979, now abandoned which in turn was a continuation of application Ser. No. 734,078, filed Oct. 20, 1976, now abandoned.

BACKGROUND OF THE INVENTION

Synthetic polymeric fibers that have physical and morphological characteristics generally similar to pulp fibers produced from natural woods have been known for approximately 10 years. Examples of such fibers are the synthetic wood pulp fibers formed of polyethylene that are sold by Crown Zellerbach under the trademark SWP.

Various methods of making synthetic wood pulp fibers are known, including (1) solution polymerization accompanied by stirring, (2) dissolving a preformed polymer and subjecting the solution to an anti-solvent, or (3) forming the polymer at the interface between liquid layers, with localized stirring provided to pull the polymers thus formed into fibrillated forms. Examples of methods of producing synthetic wood pulp fibers are disclosed in U.S. Pat. Nos. 3,560,318; 3,081,519; 3,003,912; 3,068,527; and 3,290,207; South African Pat. No. 697,432; and United Kingdom Pat. No. 1,102,342; and Netherlands patent application No. A132/48-7313173.

As used in this specification and the appended claims, the term "synthetic wood pulp fibers" means synthetic, water dispersible, thermoplastic, elongated, supple, randomly bent, polymeric fibers or fibrils generally similar in length and denier to conventional wood pulp fibers produced from naurally occurring woods. Each such "synthetic wood pulp fiber" is of irregular cross sectional shape measured at any given point along its length, and in addition is nonuniform in cross section along its length. The predominant shape of the fibers is usally rather ribbon-like.

Though synthetic wood pulp fibers are similar in length and denier to conventional wood pulp fibers, their uniformity is better and their size and shape consistency greater. Whereas, conventional wood pulp fibers have a length which varies from 0.5 mm to 5.0 mm and a coarseness of between ten and twenty decigrex synthetic wood pulp fibers have a length of from one to four millimeters and a coarseness of between three and ten decigrex (as disclosed, for example, in the section headed "Fiber Dimensions" in the September, 1974 publication by Crown Zellerbach entitled SWP).

Comparing some of the other properties of synthetic wood pulp fibers with conventional wood pulp: a conventional wood pulp fiber has from 1 to 5 times the breaking stress of synthetic wood pulp; whereas, the synthetic wood pulp fiber elongates at rupture 3 to 5 times as much as a conventional wood pulp fiber; hence, the overall toughness of a synthetic wood pulp fiber is similar to or even greater than that of a conventional wood pulp fiber (as disclosed, for example, in the section headed "Single Fiber Stress-Strain Behavior" in the September, 1974 publication by Crown Zellerbach entitled SWP).

The present invention utilizes synthetic wood pulp fibers in a high loft, low density, nonwoven fibrous material such as an air-laid web or fabric. Nonwoven materials are structures which consist of an assemblage or web of irregularly arranged fibers, joined randomly or more or less systematically by mechanical, chemical or other means. These materials are well known in the art, having gained considerable prominence within the last twenty years or so in the consumer market, the industrial commercial market and the hospital field. For example, nonwoven materials are becoming increasingly important in the textile and related fields, one reason being because of their low cost of manufacture for a given coverage as compared to the cost of more conventional textile fabrics formed by weaving, knitting or felting. Typical of their use is the production of hospital caps, dental bibs, eye pads, dress shields, shoe liners, shoulder pads, skirts, hand towels, handkerchiefs, tapes, bags, table napkins, curtains, draperies, absorbent batts, diaper facings, underpads, hospital drapes, and the like. Generally speaking, nonwoven materials are available today in a wide range of fabric weights of from as little as about 100 grains/sq. yd. to as much as about 4,000 grains/sq. yd. or even higher.

A number of processes and types of apparatus are known for producing nonwoven materials. These include (1) mechanical techniques (e.g., carding or garnetting), (2) wet laying techniques (e.g., inclined wire paper apparatus, cylinder paper apparatus, etc.) and (3) air-laying techniques. The high loft, low density, nonwoven materials such as webs or fabrics to which this invention relates may suitably be produced, in the manner to be explained in detail below, from fibrous layers manufactured by well known air-laying processes.

SUMMARY OF THE INVENTION

In the method of this invention, heat is first applied in the absence of pressure to a starting layer of irregularly arranged, intersecting, overlapping, mechanically interengaged, loosely assembled fibers that include synthetic wood pulp fibers, as well as other fibers that melt at a temperature above the melting point of the synthetic wood fibers. A self-supporting fibrous web is thereby formed, as synthetic wood pulp fibers are fused and bonded with each other and with at least some of the other fibers of the starting layer.

In the next step of the method of this invention, a latex binder is introduced into the fibrous web thus formed, preferably substantially throughout the web. The binder is then dried and cured to form a stable bonded fibrous material of good wet strength, abrasion resistance and delamination resistance, with substantially lower density and less stiffness and harshness than would be exhibited by a similarly bonded fibrous web formed of the other fibers alone. Other important advantages are achieved by the use of this method.

The starting fibrous layer may include a blend of synthetic wood pulp fibers and other fibers that is substantially uniform throughout the material. Or, if desired, various zones of the fibrous starting layer oriented parallel to the plane of the fibrous layer may contain different proportions of synthetic wood pulp fibers. If the concentration of synthetic wood pulp fibers in the starting layer is greater at or near at least one external surface of the layer, the particular properties given the layer by such a surface rich distribution of synthetic wood pulp fibers will be concentrated at or near that surface. If the concentration of synthetic wood pulp fibers in the starting layer is greater near the median plane of that layer, good delamination resistance will be produced in the resulting fibrous material while few, if any, synthetic wood pulp fibers will be located near the outer surfaces of the material.

Surprisingly, it has been found that the mere heating of the fibrous starting layer containing synthetic wood pulp fibers in the first step of the method of this invention does not produce any substantial shrinkage or undesirable stiffness of the resulting self-supporting fibrous web, as is the case with melt bonding of many other fibers employed for this purpose, such as certain polyester fibers.

Equally surprising, when the self-supporting fibrous web that has been bonded in the method of this invention by the introduction and curing of a latex binder is subjected to a step, such as creping or micropleating, that is specifically intended to produce shrinking, the resulting fibrous material of reduced dimensions is permanently shrunk. The resulting material, when pulled back in either wet or dry condition to its original length and released, will return almost to its new reduced length. As an accompanying benefit, it has been found that linting, as well as fiber loss during any such shrinking process as just mentioned, are both significantly reduced by the presence of the synthetic wood pulp fibers.

Other unexpected results from the practice of this invention include the following properties of the resulting bonded fibrous material as compared to a comparable weight dry formed latex bonded material of the same fibers without the synthetic wood pulp fibers: (1) increased web strength and wet stability in general, (2) greater delamination resistance, (3) lower bending stiffness, (4) increased liquid holding capacity, (5) greater loft, (6) greater resiliency, and (7) lower density. The wet strength of nonwoven fabrics produced by the practice of this invention has been found, for example, to be from about 60 percent to 80 percent of the dry fabric strength, compared with only 50 percent for conventionally bonded fabrics.

Some of the properties in the numbered list in the preceding paragraph, such as the last four in the list, appear to be attributable primarily to the fact that in the method of this invention, the aqueous latex binder is added only after the synthetic wood pulp fibers have been heat fused to give some structural integrity to the web, and thus the extent of wet collapse of the web during the bonding step is greatly reduced if not eliminated. Other properties such as decreased bending stiffness appear to be attributable primarily to the unexpectedly low level of latex binder that has been found to provide adequate bonding when added, in the second step of the method of this invention, to the self-supporting web stabilized with fused synthetic wood pulp fibers that is produced in the first step of the method. In other words, the stiffness that would be expected in a fabric subject to two bonding steps, one carried out with synthetic wood pulp fibers (as disclosed, for example, in the section headed "Applications—Nonwovens and Laminates" in the September, 1974 publication by Crown Zellerbach entitled SWP), and the other with conventional latex binder, surprisingly does not appear.

When the fibrous material of this invention is surface rich in synthetic wood pulp fibers, it is found that the fibrous material of this invention displays greatly increased pilling and abrasion resistance, two to six times better than with conventionally bonded fabrics. Nonwoven fabrics made by the practice of this invention that are surface rich in synthetic wood pulp fibers have also been found to exhibit good surface softness, with accompanying elimination of prickle. When the fibrous material of this invention is rich in heat fused synthetic wood pulp fibers in the midplane, the material exhibits adequate delamination strength regardless of the location of any subsequently added latex binder or any possible migration of the binder within the fibrous material.

The indicated fabric property improvements have been obtained when the other fibers of the fabric are formed, for example, of rayon or polyester, and the improvements have made possible the achievement of desirable fabric properties with the use of a substantially smaller quantity of textile fiber and/or latex binder. Surprisingly, polyester fibers are found to produce a synergistic effect with the synthetic wood pulp fibers, and as a consequence, nonwoven fabrics formed of polyester fibers have been found to have their performance characteristics brought up generally to the level of quality ordinarily found only in nonwoven fabrics formed with rayon fibers.

The materials produced in accordance with this invention are useful wherever it is desired to take advantage of their lower density and higher bulk as compared to conventional air laid fabrics and/or whenever their excellent wet strength, softness and low-linting qualities are desired. Typical applications are for surgeons' gowns and surgical drapes, non-linting wiping cloths, wound dressings, coverings for sanitary napkins, and facings for diapers. In addition, as described below, in an embodiment in which latex application is minimal, or entirely eliminated, the fabrics may be used to produce absorbent batts in diaper constructions.

BRIEF DESCRIPTION OF THE DRAWINGS

The invention will now be described with reference to the accompanying drawings, in which:

FIG. 1 is an enlarged diagrammatic representation of a portion of a fibrous layer that may be employed as the starting material for the method of this invention;

FIG. 2 is a diagrammatic side elevation view of one form of apparatus for producing the fibrous material of this invention;

FIG. 3 is an enlarged diagrammatic representation of two segments of synthetic wood pulp fibers fused together, with their junction reinforced by a small quantity of adhesive binder deposited thereon;

FIGS. 4 and 5 are fragmentary, diagrammatic representations in cross section of two embodiments of the high loft, low density, nonwoven fibrous material of this invention; and FIG. 6 is a partial cross section of a typical diaper utilizing one embodiment of the material of this invention as a facing layer and another embodiment thereof as an absorbent batt.

DETAILED DESCRIPTION OF THIS INVENTION

Starting Materials

FIG. 1 is an enlarged, diagrammatic representation of a layer 10 of irregulary arranged, intersecting, overlapping, mechanically interengaged, loosely assembled fibers that is the starting material for the method and product of this invention. Fibrous layer 10 contains at least two types of fibers. Thermoplastic synthetic wood pulp fibers 12 are drawn as dark fibers in the drawing, and the lighter fibers 14 are longer textile type fibers. Thermoplastic synthetic wood pulp fibers 12 have a great multiplicity of contact points, both with other fibers of the same kind and with different fibers throughout layer 10. The elongated configuration of the thermoplastic synthetic wood pulp fibers permits them to bridge the distance between fibers close to each other so that individual thermoplastic synthetic wood pulp fibers have a greater multiplicity of contact points in comparison with spherical thermoplastic particles.

The term "mechanically interengaged" is used in this specification and claims to refer to fibers (usually randomly bent) that are interlocked or interentangled with other fibers to provide a degree of structural integrity whether or not binder is present in the layer of fibers.

The fibers other than synthetic wood pulp fibers 12 contained in the starting material for the method and product of this invention may comprise any fibers that can be bonded to synthetic wood pulp fibers by heat fusion of the latter fibers. Such other fibers may include natural fibers such as cotton, flax, silk, wool, wood pulp, jute, etc.; artificial fibers, such as viscose rayon, ethyl cellulose or cellulose acetate; synthetic fibers such as polyamides, polyesters, acrylics, vinylidene chloride, polyvinylchloride, polyurethane, polypropylene, etc., alone or in combination with one another. Fibers 14 have a melting point, or degradation temperature, that is higher than that of synthetic wood pulp fibers 12, preferably by 10° to 20° C. or more. Fibers 14, shown in enlarged view in FIG. 1, are viscose rayon fibers approximately 1 to 2 inches in length.

A very satisfactory fibrous material according to the present invention may be produced from a fibrous starting layer in which the fibers other than synthetic wood pulp fibers are polyester fibers. When polyester fibers are employed, it is preferred to prestabilize the fibers by removing any curl present in them before they are mixed with synthetic wood pulp fibers and the mixture of fibers is heated in the method of this invention.

Relatively long textile type fibers above normal paper making lengths and close to normal textile length, say of about ⅜ inch to 2 inches or longer, are preferred for some applications. Shorter fibers below ¼ inch in length and within the paper making range may be used in other applictions. It is preferred, however, that any shorter paper making fibers employed be unbeaten or substantially unhydrated if a textile-like fibrous material is desired as the end product. Shorter wood fibers may be used to decrease the cost of the product of this invention, with longer fibers intermixed therewith to provide the strengths desired in the resulting product.

Synthetic wood pulp fibers 12 in fibrous starting material 10, shown in enlarged view in FIG. 1, have an average length of approximately 1/16 inch. They represent about 10 percent by weight of the fibrous starting material shown.

Satisfactory nonwoven fibrous materials may be produced according to this invention weighing between about 100 grains/sq. yd. and about 1200 grains/sq. yd. or even higher.

If desired, fibrous layer 10 as shown in FIG. 1 may be formed by means of an air deposition process. The left-hand portion of FIG. 2 provides a diagrammatic showing in side elevation of apparatus that may be used in this manner. The apparatus shown is similar to the web forming apparatus disclosed in commonly assigned U.S. Pat. Nos. 3,740,797 to Farrington, 3,768,118 to Ruffo, et al., and 3,772,739 to Lovgren. A board 20 of synthetic wood pulp fibers is fed into air deposition apparatus 21 between guide plate 22 and feed roll 24, into edgewise contact with lickerin 26, which separates the web into individual fibers of synthetic wood pulp. At the same time, a supply of textile length fibers in the form of carded web 29 is fed between guide plate 30 and feed roll 31 into lickerin 32, and from there the fibers are directed downward onto the upper reach of endless belt 34.

As synthetic wood pulp fibers and textile fibers are directed downward from lickerins 26 and 32, respectively, they are intermingled to form fibrous starting material 10, which moves from left to right with the endless belt in FIG. 2. The vertical location of baffle 36 determines the degree of crossover, or the relative proportions of synthetic wood pulp fibers and longer textile fibers at each thickness level that are deposited to form fibrous layer 10.

Fibrous starting layer 10 may include a substantially uniform blend of synthetic wood pulp fibers 12 and other fibers 14 throughout the material. On the other hand, air deposition apparatus 24 can be adjusted, as explained in the patents referred to above which disclose such apparatus, to produce different proportions of synthetic wood pulp fibers and other fibers in various zones of the fibrous starting layer oriented parallel to the median plane of the fibrous layer.

THE PREFERRED METHOD OF THIS INVENTION

In the first step of the preferred method of this invention, heat is applied in the absence of pressure to fibrous starting layer 10 to raise synthetic wood pulp fibers 12 to or a little above their melting point. The heat may be applied by any conventional means, as for example, by infra-red heater 40 shown diagrammatically in FIG. 2, which is positioned above fibrous layer 10 as it moves from left to right in that figure. The heating means may, if desired, be a radiant heater, or other suitable heating means. As a result of this application of heat, synthetic wood pulp fibers in layer 10 are fused to at least some of the other synthetic wood pulp fibers in the layer, and to some of the textile length fibers 14, to form a self-supporting fibrous web.

In the next step, a latex binder in the form of an emulsion or suspension is introduced into the fibrous web, thus formed. The binder may be added to the fibrous web by any conventional means such as suction bonding or spray bonding means 42 shown diagrammatically in FIG. 2. For satisfactory results, latex binder should be added sufficient to produce dried and cured binder in an amount no greater than about 6 percent of the weight of the final fibrous material produced by the practice of this invention. A softer product with slightly less structual stength is produced by the addition of latex binder sufficient to produce dried and cured binder in an amount no greater than 4 percent by weight of the final fibrous material of this invention. Still greater softness results if that figure is 2 percent by weight of the resulting fibrous material.

Because the heat fusing of synthetic wood pulp fibers 12 to each other and to textile fibers 14 in fibrous layer 10 in the first step of this method gives some structural integrity to web 10, the extent of wet collapse of the web during the bonding step is greatly reduced, if not eliminated altogether.

In the next step of the method of this invention, the adhesive binder applied to fibrous layer 10 as just described is dried and cured. This may be effected by any conventional means such as infra-red heating means 44 shown diagrammatically at the right hand end of FIG.

2. The heating means may, if desired, be a dielectric heater or other heating means. Preferably, at least a portion of the heating should be effected by use of heating means that applies heat to the midportions of fibrous layer 10, in order to avoid undue migration of binder to the external surfaces of the product.

The steps of the method described produce a stable bonded fibrous material of good wet strength, abrasion resistance and delamination resistance, with substantially lower density and less stiffness and harshness than would be exhibited by a fibrous web formed of textile fibers 14 alone and with its fibers bonded only by additional binder such as that added by spray bonding means 42. One reason for this is the unexpectedly low level of adhesive binder that has been found to provide adequate bonding, when it is added to the self-supporting web stabilized with fused synthetic wood pulp fibers as a result of the heating of fibrous layer 10 by heating means 40.

When adhesive binder is introduced into fibrous layer 10, it is preferably distributed substantially throughout the layer. The addition of the binder produces to effects that contribute to the structural integrity of the resulting fibrous material: (1) Some of the binder forms globules that cause fibers 12 and 14 to adhere to other fibers of the same type, and cause still other fibers to adhere to fibers of a different type. (2) In addition, as illustrated in FIG. 3, some globules of adhesive 50 are deposited at heat fused contact zones 52 between a synthetic wood pulp fiber 12 and another fiber which forms a part of the network of fused bonded junctures throughout the self-supporting fibrous web resulting from the first step of the method of this invention. The other fiber with which synthetic wood pulp fiber 12 is heat fused and bonded may be a textile fiber 14, as shown in FIG. 3, or may be another synthetic wood pulp fiber 12. In either event, binder globule 50 overlies and supplements juncture 52 where one fiber segment is fused with another.

VARIOUS EMBODIMENTS OF THE PRODUCT OF THIS INVENTION

FIGS. 4 and 5 provide fragmentary, diagrammatic representations in cross section of portions of the fibrous material of this invention in which the concentration of synthetic wood pulp fibers is greater in one zone of the fibrous material than in another. In FIG. 4, fibrous starting layer 60 has a higher concentration of synthetic wood pulp fibers in its midportion 62, a region parallel to the median plane of the starting layer. Zones 64 lying on either side of midportion 62 contain no synthetic wood pulp fibers in the embodiment shown, but only other fibers such as textile length fibers. The fibrous material produced from starting layer 60 by the method of this invention exhibits good resistance to delamination.

FIG. 5 gives a fragmentary, diagrammatic representation in cross section of fibrous starting material 70 in which the highest concentration of synthetic wood pulp fibers is located in region 72, adjacent one external boundary surface 74 of the layer. In the embodiment shown, midportion 76 and opposite external boundary surface portion 78 of fibrous starting layer 70 contains no synthetic wood pulp fibers. The fibrous material produced from starting layer 70 by the method of this invention exhibits good resistance to abrasion because of the heat fusion bonding of synthetic wood pulp fibers in region 72 to other such fibers and to other types of fibers, all located adjacent boundary surface 74.

It should be understood that while for purposes of clarity, FIGS. 4 and 5 show fibrous layers adjoining each other at sharply defined interfaces, in the actual product, there is a more or less gradual transition from one layer to another, with fibers intermingled as described above, as each layer merges into the adjoining layer.

A variation of the method of this invention produces a fibrous material that has a "memory" for a reduced length. In this variation of the method, the self-supporting fibrous web resulting from the first step of this invention is processed—for example, immediately after it has passed radiant heater 40 in FIG. 2 and before binder has been added by spray means 42—to reduce its length and develop an interesting surface texture. This may be accomplished by well-known methods of creping or micropleating, by means illustrated diagrammatically at 80 in FIG. 2. When the final fibrous material resulting from the completion of the method described in claim 1 is pulled back to its original length and then released, it will return almost to its reduced length.

Excellent abrasion resistance and delamination resistance is achieved with this invention utilizing a fibrous starting layer 10 in which synthetic wood pulp fibers 12 represent no more than about 30 percent by weight of the layer. If this percentage is no more than about 20 percent, good delamination and abrasion resistance are still achieved and the softness of the material increases. Satisfactory delamination and abrasion resistance are still achieved, with still greater softness in the resulting fibrous material, if starting layer 10 contains no more than about 10 percent by weight of synthetic wood pulp fibers 12.

A fibrous material exhibiting a considerable degree of water resistance can be produced by use of the method of this invention by including nonwettable synthetic wood pulp fibers in fibrous starting layer 10. Increased water resistance is achieved when the only synthetic wood pulp fibers 12 included in fibrous starting layer 10 are nonwettable, and maximum water resistance is achieved if all the fibers at an external boundary surface, such as region 72 in FIG. 5, are nonwettable synthetic wood pulp fibers. Nonwettable synthetic wood pulp fibers are formed of hydrophobic polymers, and in commercial form should be free of any surfactant film, or water soluble coating, on the external surface of the fibers.

The high loft stability obtainable by the application of heat without pressure to an air-laid web containing synthetic wood pulp fibers is useful in the production of adsorbent batt such as batts for diapers, where high liquid adsorptive capacity is desired. It is known that a high loft, low density batt is capable of holding more aqueous liquid than a more compressed batt of the same fibers at an equivalent weight. In diapers for infants, the adsorptive capacity of a diaper batt is reduced when the batt is compressed by the weight of the infant, but bonding the adsorptive fibers together through synthetic wood pulp fibers to stabilize the high loft reduces the extent of compression of the batt under the infant's weight, particularly when wet, and thereby helps to maintain maximum adsorption capacity.

Where it is desired to have the high loft material serve an adsorptive function, it is important to avoid imparting hydrophobicity to the batt fibers and to avoid treating the batt fibers with a surfactant. Therefore, for this application, the latex binder composition used is one which contains no surfactant and, to minimize the normal hydrophobicity of the latex binder, the binder treatment is the minimum treatment which will maintain the integrity of the batt.

The latex binder may be applied, for example, as a light surface spray or foam or may be applied by suction bonding at a very low level, such as as a level of 1 weight percent or less.

If desired, the latex binder treatment step may be eliminated entirely for this application, although in this case it is desirable to utilize the synthetic wood pulp fibers at a concentration in the upper portion of the aforementioned range, say between about 20 and 30 weight percent of the total fiber weight.

The reason that the latex binder treatment can be minimized or even eliminated for adsorbent application is that an adsorbent batt, sandwiched in a diaper between other elements of greater structural strength, need not have as much structural integrity or as great a resistance to linting as a material which is by itself in its ultimate application or which constitutes an external surface in its ultimate application.

FIG. 6 shows a partial cross section, a typical diaper utilizing one embodiment of the material of this invention as a facing layer and another embodiment of the material of this invention as an adsorptive batt.

The diaper of FIG. 6 is made up of three principal elements, specifically, facing layer 91, batt 92, and impervious backing sheet 93.

Facing layer 91 comprises one embodiment of the high loft, low density, nonwoven fibrous material of this invention containing thermoplastic synthetic wood pulp fibers heat fused at a plurality of junctures with segments both of thermoplastic synthetic wood pulp fibers and other fibers to form a self-supporting fibrous web and having additional binder distributed in the material to bind fiber segments with each other throughout the material. Facing layer 91 may be uniform throughout its thickness, or may have different concentrations of fibers at different depths as shown in FIGS. 4 and 5. Facing layer 91 may also be creped or micropleated, as described above, to provide extensibility in the facing layer for a better fit in the diaper.

Batt 92 comprises another embodiment of the high loft, low density, nonwoven fibrous material of this invention. It is composed primarily of short cellulose fibers, such as wood pulp fibers or cotton linters for high liquid adsorbency and low cost. It contains thermoplastic synthetic wood pulp fibers in sufficient quantity to provide, by heat fusion at a plurality of junctures with segments both of synthetic wood pulp fibers and cellulose fibers, a self-supporting web. The batt may also contain a small amount of additional binder as a residue of an applied latex or may be free of additional binder.

If desired, batt 92 may also be treated by applied moisture and pressure on its surface opposite the facing layer to produce a high density, paper-like skin which is strongly wettable and serves to draw liquid away from the area of discharge toward the edges of the diaper as disclosed in U.S. Pat. No. 3,612,055.

Impervious backing sheet 93 is preferably a plastic film such as an embossed polyethylene film and is adhered to the batt and to the facing layer by spaced adhesive bead lines 94 which are longitudinally disposed with respect to the length dimension of the diaper.

The above detailed description of this invention has been given for clarity of understanding only. No unnecessary limitations are to be understood therefrom, as modifications will be obvious to those skilled in the art.

We claim:

1. A high loft, low density, nonwoven fibrous material containing thermoplastic synthetic wood pulp fibers, as one constituent thereof and fibrous material other than thermoplastic synthetic wood pulp fibers, said synthetic wood pulp fibers having a length and denier generally similar to natural wood pulp fibers, which comprises: a plurality of irregularly arranged, intersecting, overlapping, mechanically interengaged, loosely assembled fibers including both thermoplastic synthetic wood pulp fibers and fibers other than synthetic wood pulp fibers, said fibrous material contains generally in the range of about 10 percent to about 30 percent by weight of said synthetic wood pulp fibers, said other fibers having a melting point above that of the synthetic wood pulp fibers, the general orientation and arrangement of the fibers of said material being substantially the same in all directions across the material and substantially uniform from one boundary surface of the material to the other; segments of said synthetic wood pulp fibers having been heat fused in the absence of pressure at a plurality of junctures with segments of both said synthetic wood pulp fibers and said other fibers to form a self-supporting fibrous web in the absence of any additional binder; and said web having an additional binder distributed therein to bond fiber segments in contact with each other, whereby a stable bonded fibrous material is provided having good wet strength and delamination resistance, with substantially lower density and less shrinkage stiffness, harshness and evidence of web collapse than would be exhibited by a fibrous web formed of said other fibers alone and with its fibers bonded only by said additional binder.

2. The fibrous material of claim 1 in which said additional binder is distributed substantially throughout said fibrous material.

3. The fibrous material of claim 1 in which portions of said additional binder overlie and supplement at least some of the junctures where segments of said synthetic wood pulp fiber segments are heat fused with other fiber segments.

4. The fibrous material of claim 1 which includes a substantially uniform blend of said synthetic wood pulp fibers and said other fibers throughout the material.

5. The fibrous material of claim 1 in which various zones oriented parallel to the median plane of the fibrous material contain different proportions of said synthetic wood pulp fibers.

6. The fibrous material of claim 5 in which the concentration of said synthetic wood pulp fibers in said fibrous material is greater adjacent at least one external boundary surface of the material than in the midportion thereof lying between its two external boundary surface portions, whereby said material exhibits good resistance to abrasion.

7. The fibrous material of claim 5 in which the concentration of said synthetic wood pulp fibers in said fibrous material is greater in its midportion in a region parallel to the median plane of the material, whereby said material exhibits good resistance to delamination.

8. The fibrous material of claim 1 in which said other fibers are rayon fibers.

9. The fibrous material of claim 1 in which said other fibers are polyester fibers.

10. The fibrous material of claim 1 in which said other fibers are polypropylene fibers.

11. The fibrous material of claim 9 in which said polyester fibers are substantially free of any curl along their longitudinal axes.

12. The fibrous material of claim 1 which has been shrunk to reduce its length and to develop surface texture therein, whereby when said fibrous material is pulled back to its original length and released, it will return almost to its said reduced length.

13. The fibrous material of claim 12 which is creped.

14. The fibrous material of claim 12 which is micropleated.

15. The fibrous material of claim 1 which contains no more than about 20 percent by weight of said synthetic wood pulp fibers.

16. The fibrous material of claim 1 which contains no more than about 10 percent by weight of thermoplastic synthetic wood pulp fibers.

17. The fibrous material of claim 1 in which said additional binder is a latex binder and is present in an amount equal to no more than about 6 percent by weight of said material.

18. The fibrous material of claim 1 in which said additional binder is a latex binder and is present in an amount equal to no more than about 4 percent by weight of said material.

19. The fibrous material of claim 1 in which said additional binder is a latex binder and is present in an amount equal to no more than about 2 percent by weight of said material.

20. The fibrous material of claim 1 which includes both wettable and nonwettable thermoplastic synthetic wood pulp fibers.

21. The fibrous material of claim 1 in which the only thermoplastic synthetic wood pulp fibers included in the material are nonwettable.

22. The fibrous material of claim 1 in which all the fibers adjacent at least one external boundary surface of said material are nonwettable thermoplastic synthetic wood pulp fibers.

23. In a diaper structure comprising a facing layer, an adsorbent batt and an impervious backing layer in which said facing layer and said backing sheet are outermost layers and said batt is positioned between said facing layer and said backing sheet, the improvement wherein said facing layer comprises the high loft, low density, nonwoven fibrous material of claim 1.

24. The diaper structure of claim 23 wherein said facing layer comprises a substantially uniform blend of said synthetic wood pulp fibers and other fibers throughout the material.

25. The diaper structure of claim 23 wherein, in said facing layer, various zones oriented parallel to the median plane of the layer contain different proportions of said synthetic wood pulp fibers.

26. The fibrous material of claim 1 in which said binder is present in an amount in the range of about 2 percent to about 6 percent by weight of said material.

27. A method of producing a high loft, low density, nonwoven fibrous material containing thermoplastic synthetic wood pulp fibers as one constituent thereof and fibrous material other than thermoplastic synthetic wood pulp fibers, said thermoplastic synthetic wood pulp fibers having a length and denier generally similar to natural wood pulp fibers, which comprises:

applying heat in the absence of pressure to a starting layer of irregularly arranged, intersecting, overlapping, mechanically interengaged, loosely assembled fibers including both said synthetic wood pulp fibers and fibers other than synthetic wood pulp fibers, said fibrous material contains generally in the range of about 10 percent to about 30 percent by weight of said synthetic wood pulp fibers, the general orientation and arrangement of the fibers of said material being substantially the same in all directions across the material and substantially uniform from one boundary surface of the material to the other, said other fibers having a melting point, or degradation temperature, above that of the temperature of the synthetic wood pulp fibers, to fuse at least some of said synthetic wood pulp fibers to each other and to some of said other fibers and thereby form a self-supporting fibrous web in the absence of any additional binder which is resistant to web collapse during the subsequent bonding step;

introducing a liquid binder into said fibrous web; and drying and curing said binder to bond fiber segments in contact with each other throughout the web to form a stable bonded fibrous material of good wet strength, abrasion resistance and delamination resistance with substantially lower density and less shrinkage stiffness and harshness than would be exhibited by a fibrous web formed of said other fibers alone and with its fibers bonded only by said binder.

28. The method of claim 27 in which said binder is added to said fibrous web in an amount in the range of about 2 percent to about 6 percent by weight of the bonded fibrous layer when said binder has been dried and cured.

29. The method of claim 28 in which said binder is a latex binder and when it is introduced into said fibrous layer, it is distributed substantially throughout said layer.

30. The method of claim 27 in which said starting fibrous layer includes a substantially uniform blend of said synthetic wood pulp fibers and said other fibers throughout the material.

31. The method of claim 27 in which various zones of said fibrous starting layer oriented parallel to the median plane of the fibrous layer contain different proportions of said synthetic wood pulp fibers.

32. The method of claim 31 in which the concentration of said synthetic wood pulp fibers in said starting layer of fibers is greater adjacent at least one external boundary surface thereof than in the midportion of the layer lying between its two external boundary surface portions.

33. The method of claim 31 in which the concentration of said synthetic wood pulp fibers in said starting layer of fibers is greater in its midportion in a region parallel to the median plane of the starting layer.

34. The method of claim 27 in which said other fibers are rayon fibers.

35. The method of claim 27 in which said other fibers are polyester fibers.

36. The method of claim 27 in which said other fibers are polyethylene fibers.

37. The method of claim 35 in which said polyester fibers are prestabilized by removing any curl present therein before they are mixed with said synthetic wood pulp fibers and said mixture is heated.

38. The method of claim 27 in which said self-supporting fibrous web is shrunk after its formation in the heating step and before the binder adding step as described in said claim, to reduce the length of said web and develop surface texture therein, whereby when the final fibrous material resulting from the completion of the method described in claim 1 is pulled back to its original length and then released, it will return almost to its said reduced length.

39. The method of claim 38 in which said shrinking step is effected by a creping process.

40. The method of claim 38 in which said shrinking step is effected by a micropleating process.

41. The method of claim 27 in which said starting layer of fibers contains no more than about 20 percent by weight of said synthetic wood pulp fibers.

42. The method of claim 27 in which said starting layer of fibers contains no more than about 10 percent by weight of thermoplastic synthetic wood pulp fibers.

43. The method of claim 27 in which said binder is added to said fibrous web in an amount equivalent to no more than about 6 percent by weight of the bonded fibrous layer when said binder has been dried and cured.

44. The method of claim 27 in which said binder is added to said fibrous web in an amount equivalent to no more than about 4 percent by weight of the bonded fibrous layer when said binder has been dried and cured.

45. The method of claim 27 in which said binder is added to said fibrous web in an amount equivalent to no more than about 2 percent by weight of the bonded fibrous layer when said binder has been dried and cured.

46. The method of claim 27 in which said starting layer of fibers includes both wettable and nonwettable thermoplastic synthetic wood pulp fibers.

47. The method of claim 27 in which the only thermoplastic synthetic wood pulp fibers included in said starting layer of fibers are nonwettable.

48. The method of claim 27 in which all the fibers adjacent at least one external boundary surface of said starting layer are nonwettable thermoplastic synthetic wood pulp fibers.

* * * * *